United States Patent [19]
Berg et al.

[11] Patent Number: 6,068,654
[45] Date of Patent: May 30, 2000

[54] T-SHAPED MEDICAL GRAFT CONNECTOR

[75] Inventors: Todd A. Berg, Lino Lakes; Daniel J. Sullivan, Medina, both of Minn.

[73] Assignee: Vascular Science, Inc., Minneapolis, Minn.

[21] Appl. No.: 08/996,981

[22] Filed: Dec. 23, 1997

[51] Int. Cl.⁷ .................................................. A61F 2/06
[52] U.S. Cl. .............................. 623/1; 623/12; 606/153; 606/191
[58] Field of Search .......................... 623/1, 12; 606/153, 606/191, 195, 198

[56] References Cited

U.S. PATENT DOCUMENTS

| | | | |
|---|---|---|---|
| 4,214,587 | 7/1980 | Sakura, Jr. | 128/334 |
| 4,503,569 | 3/1985 | Dotter | 3/1.4 |
| 4,592,754 | 6/1986 | Gupte et al. | 623/1 |
| 4,617,932 | 10/1986 | Kornberg | 128/334 R |
| 4,665,906 | 5/1987 | Jervis | 128/92 YN |
| 4,739,762 | 4/1988 | Palmaz | 623/1 |
| 4,787,899 | 11/1988 | Lazarus | 623/1 |
| 5,104,399 | 4/1992 | Lazarus | 623/1 |
| 5,135,467 | 8/1992 | Citron | 600/16 |
| 5,211,658 | 5/1993 | Clouse | 623/1 |
| 5,211,683 | 5/1993 | Maginot | 128/898 |
| 5,275,622 | 1/1994 | Lazarus et al. | 623/1 |
| 5,304,220 | 4/1994 | Maginot | 623/1 |
| 5,316,023 | 5/1994 | Palmaz et al. | 128/898 |
| 5,354,336 | 10/1994 | Kelman et al. | 623/6 |
| 5,387,235 | 2/1995 | Chuter | 623/1 |
| 5,397,345 | 3/1995 | Lazarus | 623/1 |
| 5,443,497 | 8/1995 | Venbrux | 623/1 |
| 5,456,712 | 10/1995 | Maginot | 623/1 |
| 5,489,295 | 2/1996 | Piplani et al. | 623/1 |
| 5,507,769 | 4/1996 | Marin et al. | 606/198 |
| 5,522,880 | 6/1996 | Barone et al. | 623/1 |
| 5,545,214 | 8/1996 | Stevens | 623/2 |
| 5,653,743 | 8/1997 | Martin | 623/1 |
| 5,653,747 | 8/1997 | Dereume | 623/1 |
| 5,695,504 | 12/1997 | Gifford, III et al. | 606/153 |
| 5,728,131 | 3/1998 | Frantzen et al. | 623/1 |
| 5,755,778 | 5/1998 | Kleshniski | 623/1 |

FOREIGN PATENT DOCUMENTS

| | | |
|---|---|---|
| 670 239 | 11/1996 | Australia . |
| 0 539 237 A1 | 4/1993 | European Pat. Off. . |
| 0 637 454 A1 | 2/1995 | European Pat. Off. . |
| 0 680 734 A2 | 11/1995 | European Pat. Off. . |
| 0 684 022 A2 | 11/1995 | European Pat. Off. . |
| 692923 | 10/1979 | U.S.S.R. ................... 623/1 |
| WO 96/18361 | 6/1996 | WIPO . |
| WO 97/13463 | 4/1997 | WIPO . |
| WO 97/13471 | 4/1997 | WIPO . |

*Primary Examiner*—Paul B. Prebilic
*Attorney, Agent, or Firm*—Fish & Neave; Jeffrey H. Ingerman; Joel Weiss

[57] ABSTRACT

A two-piece graft connector having a tubular band section with its proximal end configured to attach to a tubular graft and retention loops extending from its distal end, and a tubular anchor structure configured to be placed in the patient's tubular body tissue structure is provided. In a preferred embodiment, the proximal end of the tubular band section is attached to a tubular graft. The retention loops extend from the distal end of the tubular band section of the connector, through an aperture in the side wall of a patient's tubular body tissue structure. The tubular anchor structure is placed in the patient's tubular body tissue structure, within the retention loops. Then, the tubular anchor structure is circumferentially expanded, firmly retaining the retention loops, and forming a seal between the tubular band section and the side wall of the tubular body tissue structure. Alternatively, the retention loops may be replaced by retention fingers, which form arcs. When deployed, the retention fingers extend only partially around the tubular body structure, but perform substantially the same function as the retention loops. The tubular band section may be replaced as well by a tubular graft with a wire frame allowing the retention loops, or fingers, to be affixed to the wire frame.

21 Claims, 6 Drawing Sheets

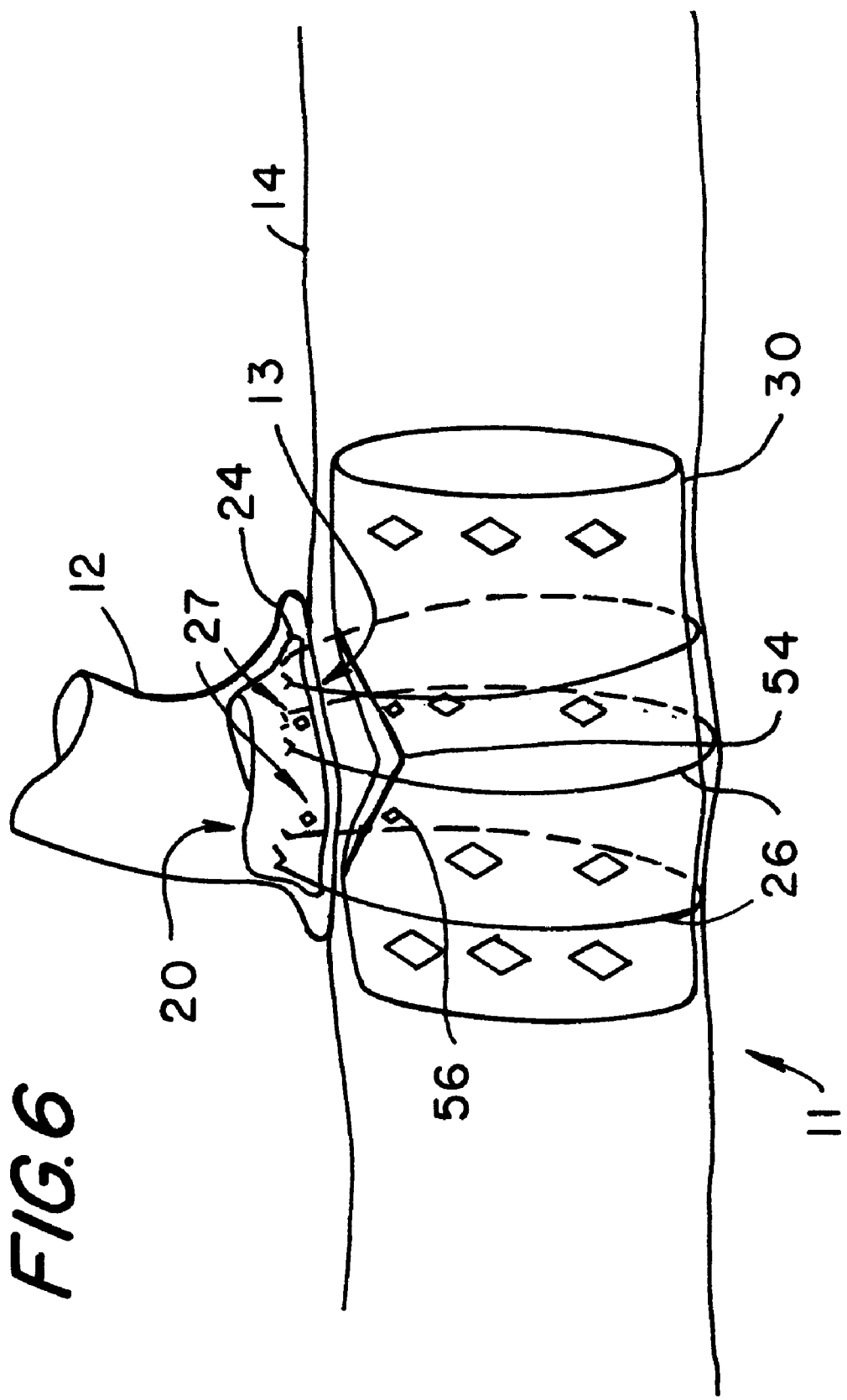

T-SHAPED MEDICAL GRAFT CONNECTOR

BACKGROUND OF THE INVENTION

This invention relates to tubular medical grafts, and more particularly to connectors for use in making tubular connections between tubular grafts and a patient's tubular tissue structures.

Goldsteen et al. U.S. patent application Ser. No. 08/745,618, filed Nov. 7, 1996, Sullivan et al. U.S. patent application Ser. No. 08/844,992, filed Apr. 23, 1997, and Sullivan et al. U.S. patent application Ser. No. 08/869,808, filed Jun. 5, 1997 (all of which are hereby incorporated by reference herein) show examples of medical procedures in which it is necessary to make one or more tubular connections between a patient's tubular body tissue structures and a tubular graft. The tubular graft may be either natural body tissue relocated from elsewhere in the patient's body, an artificial graft structure, or a combination of natural and artificial structures. In the exemplary procedures shown in the three references mentioned above it is typically necessary to connect an end of the graft to a side wall of the patient's pre-existing body tubing (e.g., a blood vessel). The three aforementioned patent applications deal primarily with procedures that are performed to the greatest extent possible percutaneously and through lumens of a patient's tubular body structures. Thus a graft connector is sometimes needed that can be delivered and installed via such lumens. It is preferable that in such a graft connector a minimum of hardware be required to pass through the aperture in the side wall of the patient's tubular body structure to engage the graft connector, because hardware passing through an artificially created aperture can damage the aperture, or widen it more than necessary. At other times, a graft connector is needed that can be installed during more traditional surgical procedures.

It is important for a graft connector to be easy and quick to install (whether percutaneously or surgically), but to be secure after installation. It is typically preferable for a graft connector to be relatively flexible after installation so that it does not form an unnaturally rigid structure in the patient's body.

In view of the foregoing, it would be desirable to be able to provide an improved graft connector for making a tubular connection between a tubular graft and a patient's tubular body tissue structures.

It would also be desirable to be able to provide a tubular graft connector that is easy and quick to install, in some cases percutaneously and in some cases surgically, but which is strong and secure after installation.

It would further be desirable to be able to provide a tubular graft connector that can be installed with a minimum of hardware passing through the aperture in the side wall of the tubular body structure to which the tubular graft is being attached.

SUMMARY OF THE INVENTION

It is an object of this invention to provide an improved graft connector for making a tubular connection between a tubular graft and a patient's tubular body tissue structures.

It is also an object of this invention to provide a tubular graft connector that is easy and quick to install, in some cases percutaneously and in some cases surgically, but which is strong and secure after installation.

It is a further object of this invention to provide a tubular graft connector that can be installed with a minimum of hardware passing through the aperture in the side wall of the tubular body structure to which the tubular graft is being attached.

These and other objects of the invention are accomplished in accordance with the principles of the invention by providing a two-piece graft connector structure for making an end-to-side connection between an end of a tubular graft and a side wall of a patient's tubular body structure. The graft connector has a tubular band section configured to make a tubular connection to the end of the tubular graft, the tubular band section having a distal end and a plurality of retention loops attached to the tubular band section, each of the retention loops having a circumference, and a tubular anchor structure configured to be inserted substantially coaxially in the patient's tubular body structure and through the retention loops, the tubular anchor structure having a side wall with a circumference which is expandable to approximately at least the circumference of the retention loops, and preferably to the circumference of the tubular body structure. In one embodiment of the invention, the loops may be replaced by arc-shaped retention fingers. These retention fingers preferably perform a function similar to the loops, as will be explained.

The retention loops of the tubular band section are preferably inserted into an aperture in the side wall of the patient's tubular body structure. The planes formed by the retention loops are preferably oriented substantially perpendicularly to the longitudinal axis of the tubular body structure. However, the retention loops need not necessarily be oriented with their planes perpendicular to the longitudinal axis. They may be oriented with their planes off-axis, as long as they are sufficiently off-axis to present an effective opening size large enough to accommodate the diameter of the unexpanded tubular anchor structure so that it can be inserted into the retention loops.

Next, the tubular anchor structure is inserted substantially coaxially in the patient's tubular body structure, adjacent to the aperture in the side wall of the tubular body structure and within the retention loops. After the tubular anchor structure is inserted into the tubular body structure and within the retention loops, it is preferably circumferentially expanded so as to engage the retention loops. More preferably, the tubular anchor structure is expanded sufficiently to compress the loops against the side wall of the patient's tubular body structure to avoid obstructing fluid flow through the tubular body structure. Also, the tension on the loops caused by the expansion of the tubular anchor structure draws the tubular graft to the patient's tubular body structure, preferably forming a seal between either the tubular graft or the tubular band section and the patient's tubular body structure.

The tubular band section of the graft connector fits around or inside an end portion of the tubular graft and may be attached before or after the distal end of the tubular band section is secured within the patient's tubular body structure by the tubular anchor structure.

In another embodiment of the invention, tubular body structure may be replaced by a tubular graft having a wire frame. This construction allows the retention loops to be welded or affixed by some suitable means directly to tubular graft without requiring an additional piece of material, i.e., the aforementioned tubular band section.

BRIEF DESCRIPTION OF THE DRAWINGS

The above and other objects and advantages of the present invention will be apparent upon consideration of the following detailed description, taken in conjunction with the accompanying drawings, in which like referenced characters refer to like parts throughout, and in which:

FIG. 6 is an elevational view, partly in section, of a second preferred embodiment of a two-piece connector according to the present invention;

DETAILED DESCRIPTION OF THE PREFERRED EMBODIMENTS

Figure 1:
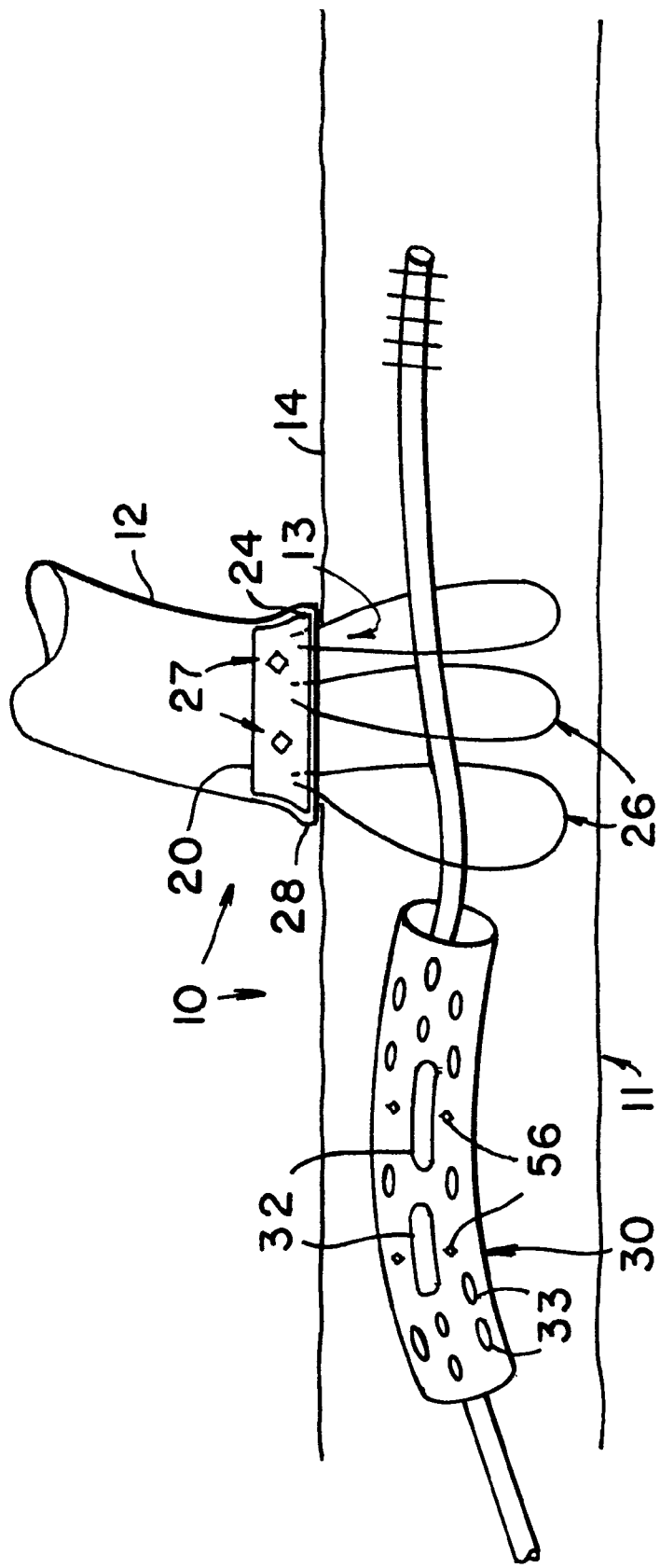
FIG. 1 is an elevational view, partly in section, of a two-piece connector according to the present invention being deployed in a tubular body structure.

An illustrative embodiment of a two-piece graft connector 10 in accordance with this invention for connecting the end of a tubular graft 12 to an aperture 13 in the side wall 14 of a patient's tubular body tissue structure 11 is shown in FIG. 1. Connector 10 preferably includes a tubular band section 20 adapted to be received in or around an end of a tubular graft 12. A plurality of retention loops 26 preferably extend from a preferably circumferential line of attachment on tubular band section 20.

Figure 8:
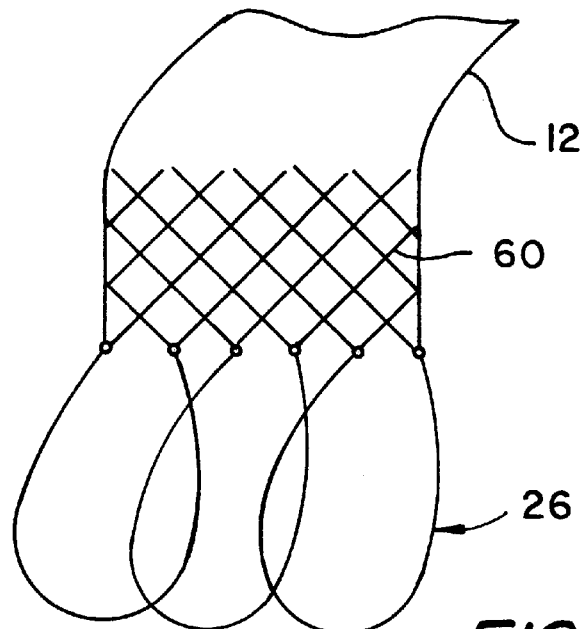
FIG. 8 is an elevational view of second preferred embodiment of the tubular band section of the two-piece connector according to the invention.
Figure 9:
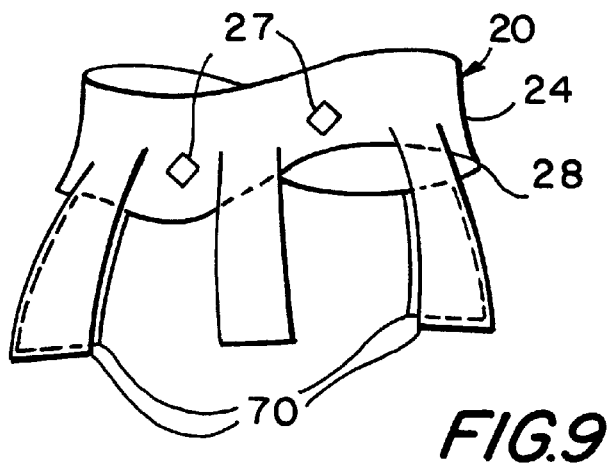
FIG. 9 is an elevational view of third preferred embodiment of the tubular band section of the two-piece connector according to the invention.

An advantage to affixing retention loops 26 to tubular band section 20 is that once tubular band section 20 is affixed to tubular graft 12, retention loops 26 cannot rotate relative to tubular graft 12. Alternatively, when tubular graft 12 is constructed from artificial tubing, a wire frame 60 may be constructed as part of the structure of tubular graft 12, as shown in FIG. 8. Retention loops 26 may then be welded or affixed by some other suitable means to wire frame 60 within tubular graft 12. In another embodiment of the invention, retention loops 26, may be replaced by relatively thicker retention fingers 70, as shown in FIG. 9. Retention fingers 70 function similarly to retention loops 26, as will be explained, but do not form loops. Rather, they form arcs, extending partially around the circumference of tubular body structure 11. Retention fingers 70 may be formed by suitable methods known in the art.

Figure 10:
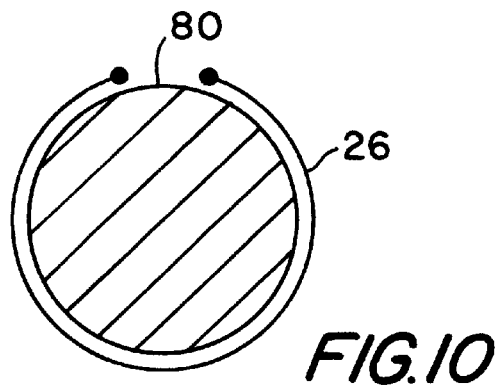
FIG. 10 is a sectional view of a retention loop according to the invention.

Nitinol wire with a diameter preferably between about 0.002 inch (about 0.05 mm) and about 0.005 inch (about 0.13 mm), or some other suitable material, may preferably be used to form retention loops 26. Retention loops 26 may preferably be heat-formed around a mandrel 80, as shown in FIG. 10. Mandrel 80 is preferably sized to approximately simulate patient's tubular body structure 11. After formation on mandrel 80, the final diameter of retention loops 26 preferably approximately matches the diameter of tubular body structure 11.

Figure 2:
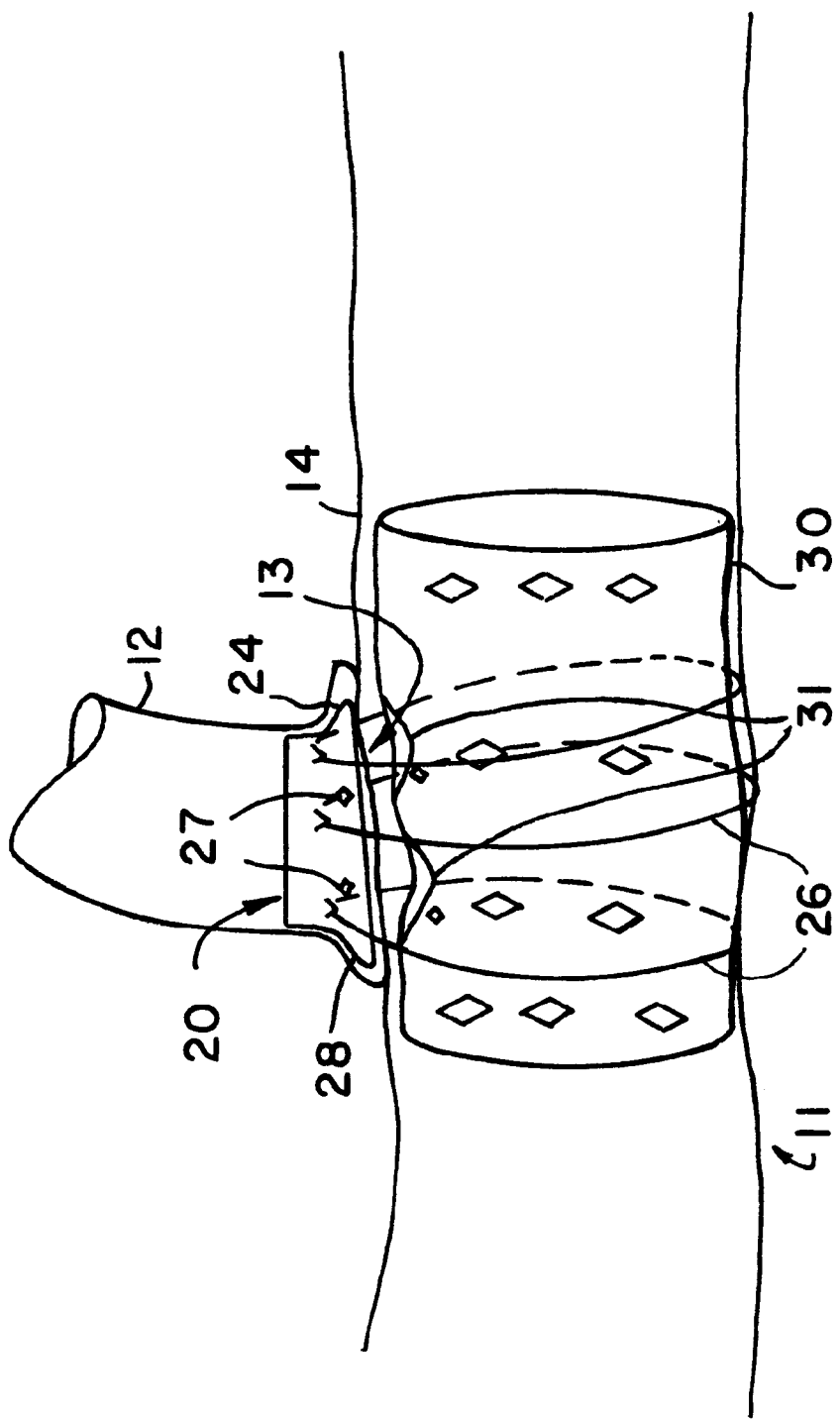
FIG. 2 is an elevational view, partly in section, of the two-piece connector of FIG. 1 after deployment is complete.
Figure 3:
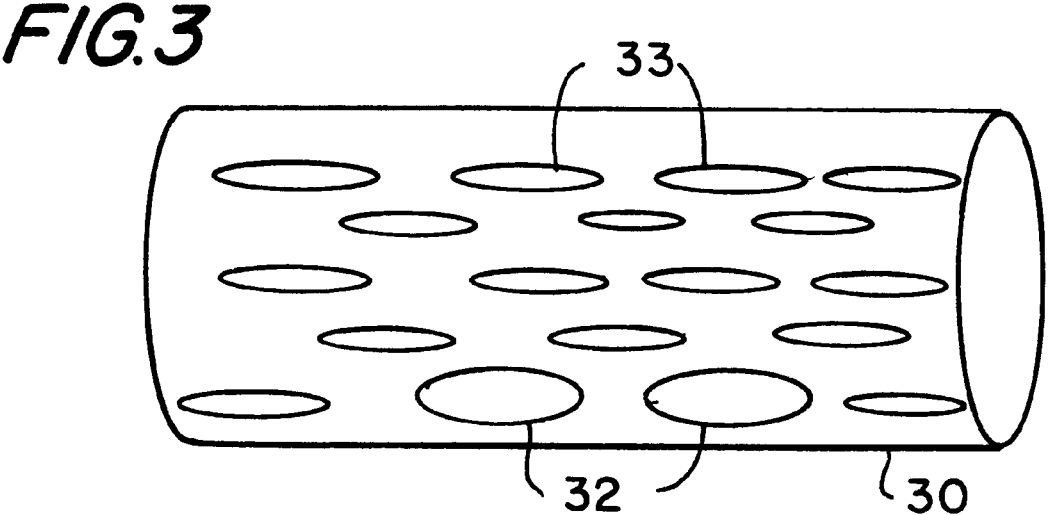
FIG. 3 is an elevational view of a preferred embodiment of a tubular anchor structure of the two-piece connector according to the invention.
Figure 4:
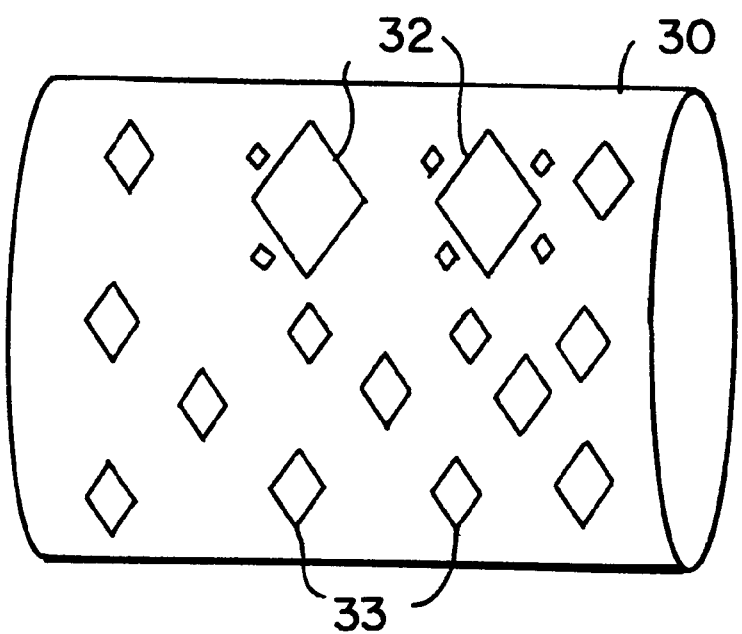
FIG. 4 is an elevational view of the tubular anchor structure of FIG. 3 in an expanded state.
Figure 5:
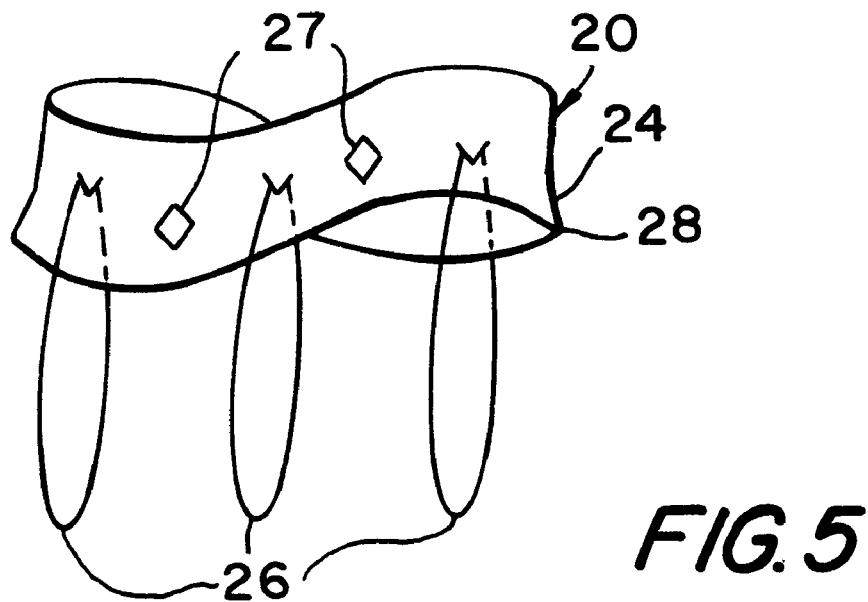
FIG. 5 is an elevational view of a first preferred embodiment of the tubular band section of the two-piece connector according to the invention.

In one embodiment of the invention, extra material extends from distal end 24 of tubular band section 20 and from tubular graft section 12 past the circumferential line of attachment of retention loops 26, forming a lip 28 around distal end 24 of tubular band section 20, as shown in FIGS. 1–2, 5 and 6, for reasons that will be explained. Connector 10 also includes a tubular anchor structure 30 which initially has a relatively small cross section as shown in FIGS. 1 and 3, but which is circumferentially expandable or enlargeable to a relatively large cross section as shown in FIGS. 2, 4, and 6.

Tubular band section 20 is preferably inserted by methods described in above-incorporated patent application Ser. No. 08/745,618. It can be attached to tubular graft 12 by a suitable method known to one skilled in the art. Although tubular graft 12 is preferably attached to tubular band section 20 before tubular band section 20 is anchored to tubular body structure 11, tubular band section 20 may be anchored to tubular body structure 11 first, and tubular band section 20 attached to tubular graft 20 afterwards. Retention loops 26 preferably extend through the aperture 13 in side wall 14 of the patient's tubular body tissue structure as shown in FIG. 1. The plane formed by each of the retention loops 26 is preferably oriented substantially perpendicularly to the longitudinal'axis of tubular body structure 11. For example, radiologic markers 27 equally spaced along the circumference of distal end 24 of tubular band section 20. These can be viewed radiologically by the physician to allow him or her to determine and adjust the orientation of tubular band section 20 with respect to tubular body structure 11, so that retention loops 26 are properly oriented.

Tubular anchor structure 30 is preferably inserted in its relatively small cross-sectional configuration (FIGS. 1 and 3) coaxially into patient's tubular body structure 11. When in its unexpanded state, tubular anchor structure 30 can be deployed percutaneously by methods described in above-incorporated application Ser. No. 08/745,618. Tubular anchor structure 30 may be delivered through tubular body structure 11. Alternatively, tubular anchor structure 30 may be delivered through tubular graft 12 and into aperture 13 in side wall 14 of patient's body tissue structure 11.

When initially deployed, tubular anchor structure 30 is preferably positioned substantially opposite aperture 13 in side wall 14, running through retention loops 26. It is for this reason that the planes of retention loops 26 are preferably oriented substantially perpendicularly to the longitudinal axis of tubular body structure 11. However, as long as each of the planes is sufficiently off-axis for tubular anchor structure 30 to be inserted through retention loops 26—the specific permissible orientation angle is a function of the diameter of tubular anchor structure 30 in its unexpanded state and of the diameter of the retention loops 26—that is all that is required.

The presence of tubular anchor structure 30 in retention loops 26 prevents removal of tubular band section 20 from tubular body structure 11. Next, tubular anchor structure 30 should preferably be circumferentially expanded so that it annularly engages retention loops 26, thus pulling on tubular band section 20 and securing the distal end 24 of tubular band section 20 to side wall 14 of patient's tubular body tissue structure 11. A preferred method of circumferentially expanding tubular anchor structure 30 is by inserting a balloon (not shown) within tubular anchor structure 30, and dilating the balloon. The balloon forces tubular anchor structure 30 into its expanded size. Following expansion, the balloon can be deflated and removed. The tubular anchor structure 30 is preferably formed from tubular metal mesh and will retain its expanded shape. Small slit-like perforations 33 in tubular anchor structure 30, which allow tubular anchor structure 30 to be expanded, are shown in FIGS. 1–4, and 6. After tubular anchor structure 30 is expanded and forms a substantially stiff, inelastic tubular structure, it preferably firmly engages retention loops 26 as shown in FIG. 2, and preferably presses closely against the inner wall of tubular body structure 11 to minimize obstruction of fluid flow.

When tubular anchor structure 30 firmly engages retention loops 26, lip 28 of tubular band section 20 preferably is drawn to aperture 13 in side wall 14, and preferably forms a hemodynamic seal between tubular band section 20 and side wall 14. Once the seal has been formed, flow between tubular graft 12 and tubular body structure 11 may continue without leakage between the two structures. Lip 28 forms the hemodynamic seal with tubular body structure 11 when tubular band section 20 is within or around (not shown) tubular graft 12. However, if tubular band section 20 is within graft 12, a lip of the material of tubular graft 12 may also help form a seal against tubular body structure 11 as shown in FIGS. 1–2 and 6. If tubular graft 12 is a natural body tissue, it may ultimately grow into tubular body structure 11, forming an even better seal.

In one embodiment of the invention, retention fingers 70 extend from the point of attachment on the tubular band section 20, as shown in FIG. 9. Each of retention fingers 70 preferably extends on one side of the tubular anchor structure 30 sufficient to reach the point of greatest width of tubular anchor structure 30. When fully deployed, tubular anchor structure 30 preferably secures retention fingers 70 within tubular body structure 11 by compressing retention fingers against side wall 14 of tubular body structure 11 (not shown). This, in turn, secures tubular graft 12 to tubular body structure 11. Retention fingers 70 may be made of nitinol or some other suitable material. Retention fingers preferably have a thickness of about 0.002 inch (about 0.05 mm), and a width of between about 0.02 inch (about 0.5 mm) and about 0.03 inch (about 0.75 mm). Retention fingers 70 are also substantially stiffer than retention loops 26 would be.

As shown in FIG. 3, tubular anchor structure 30 may be a modified metal tube, formed from expandable metal—i.e., metal that has been perforated and cut in such a way that it can be expanded in one or more directions by deforming the metal in the vicinity of the cuts and perforations. This type of structure is frequently found in stents used to prevent collapses of tubular body structures, and tubular anchor structure 30 could be a converted stent, possibly with some modifications.

Tubular anchor structure 30 is preferably circumferentially expandable by a selectively inflatable balloon. The expanded shape of tubular anchor structure 30 is shown in FIGS. 2, 4, and 6. One or more large perforations 32 may preferably be provided to provide a less obstructed flow of fluid between tubular body structure 11 and tubular graft 12. Alternatively, a single large opening 54 (See FIGS. 6, 7) may be provided for that purpose. Radiologic markers 56 are preferably provided and are preferably equally spaced along the circumference of perforations 32, or in the alternative along the circumference of opening 54, to help the physician position the tubular anchor structure 30 so that the perforations 32, or in the alternative the opening 54, faces the tubular band section 20. The radiologic markers 56 can be viewed radiologically by the physician to determine the orientation of tubular anchor structure 30 relative to the radiologic markers 27 along the circumference of distal end 24 of tubular band section 20 (FIGS. 1 and 6). This orientation procedure helps the physician maximize flow from tubular graft 12 into aperture 13. Another possible method of orienting the tubular anchor structure 30 is by delivering it through the tubular graft 12 with the perforations 32, or the opening 54, facing tubular band section 20 upon deployment. This orientation is possible because tubular anchor structure 30 is being deployed directly through tubular graft 12, and as oriented can be controlled directly and continuously during deployment.

Figure 7:
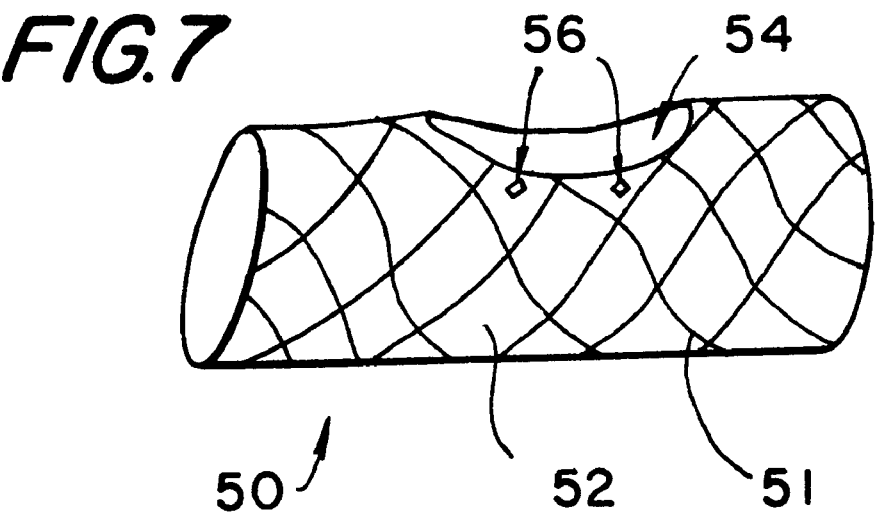
FIG. 7 is an elevational view of another preferred embodiment of a tubular anchor structure of the two-piece connector according to the present invention.

In another embodiment of the invention, tubular anchor structure 50 may be constructed from an open mesh framework 51 (e.g., a braid of nitinol, stainless steel, or tungsten wires or polymer strands) which may be covered with a rubber-like web 52 (e.g., of silicone), as shown in FIG. 7. Preferably, a large perforation 54 will be in open mesh framework 51 and rubber-like web 52, to allow for fluid flow from the tubular graft. This structure is preferably similar to tubular structures described in above-incorporated application Ser. No. 08/745,618, but is preferably made of a heavier gauge nitinol wire so that it is stiffer, to better anchor tubular band section 20. Moreover, tubular anchor structure 50 may be deployed by methods similar to those shown in said application Ser. No. 08/745,618.

An advantageous characteristic of the abovedescribed framework is that it is extremely elastic and resilient. Thus it can be radically deformed (e.g., during installation and before tubular anchor structure 50 is expanded), and it thereafter returns to its original shape without any damage or memory that it was deformed. This type of structure is also flexible in use so that it may advantageously pulse in response to blood pressure pulses when it is used in a patient's circulatory system. In other words, the connector is compliant under blood pressure. Tubular anchor structure may also be constructed in conformance with stent technology (not shown) as is known in the art.

Thus a two-piece graft connector for making end-to-side connections between the end of a graft conduit and a side wall of a patient's body structure has been provided. It will be understood that the forgoing is only illustrative of the principles of the invention and that various modifications can be made by those skilled in the art without departing from the scope and spirit of the invention.

What is claimed is:

1. A connector for making a connection between an end of a first tubular structure in a patient and a side wall of a second tubular structure in a patient comprising:

a plurality of retention elements for attachment to the first tubular structure; and a tubular anchor structure for insertion in the second tubular structure along a longitudinal axis of the second tubular structure and through said retention elements, such that at least one of said retention elements at least partially annularly engages said tubular anchor structure around a substantial portion of an outside of said tubular anchor structure.

2. The connector of claim 1 wherein said retention elements comprise loops.

3. The connector of claim 2 further comprising a tubular band section, said loops being attached to said tubular band section, said tubular band section being configured to make a tubular connection to the first tubular structure.

4. The connector of claim 3 further comprising a lip extending from said tubular band section, whereby when said tubular anchor structure retains said loops within the second tubular structure, said lip forms a seal with the second tubular structure.

5. The connector of claim 2 wherein the first tubular structure includes a wire frame, said loops being attached to said wire frame.

6. The connector of claim 1 wherein the diameter of said tubular anchor structure when deployed is at least about as great as the diameter of the second tubular structure.

7. The connector of claim 6 wherein each of said retention elements comprises a finger, said finger extending from a circumferential line of attachment on the first tubular structure for a distance sufficient to reach a point of greatest width in said tubular anchor structure.

8. The connector of claim 7 further comprising a tubular band section, each of said fingers being attached to said tubular band section, said tubular band section being configured to make a tubular connection to the first tubular structure.

9. The connector of claim 7 wherein the first tubular structure includes a wire frame, each of said retention fingers being attached to said wire frame.

10. The connector of claim 6 wherein the tubular anchor structure is radially expandable, said diameter of said tubular anchor structure before and during deployment being substantially less than said diameter of the second tubular structure.

11. The connector of claim 10 wherein said tubular anchor structure compresses said retention elements between said tubular anchor structure and the second tubular structure.

12. The connector of claim 1 wherein said elements are heat-formed around a mandrel having approximately the diameter of the second tubular structure.

13. The connector of claim 1 wherein, when said connector is deployed, each of said elements defines a plane, each of said planes running substantially perpendicular to said longitudinal axis of the second tubular structure.

14. The connector of claim 13 wherein said tubular anchor structure compresses said retention elements between the tubular anchor structure and said second tubular structure.

15. The connector of claim 1 wherein said tubular anchor structure includes a perforated tubular wall.

16. The connector of claim 8 further comprising a lip extending from said tubular band section, such that when said tubular anchor structure retains said fingers within the second tubular structure, said lip forms a seal with the second tubular structure.

17. The connector of claim 1 further comprising a lip extending from the first tubular structure, such that when said tubular anchor structure retains said retention elements within the second tubular structure, said lip forms a seal with the second tubular structure.

18. The connector of claim 15 wherein said tubular anchor structure has an opening at a junction between said tubular anchor structure and the first tubular structure, said opening having a diameter on the order of the diameter of the first tubular structure.

19. The connector of claim 18 wherein said diameter of said opening is substantially equal to said diameter of the first tubular structure.

20. The connector of claim 15 wherein said tubular anchor structure has an inner face and is formed from a tube of metal substantially completely perforated with offset slits such that pressure applied to said inner face causes said tubular anchor structure to expand and form a substantially rigid tubular mesh.

21. The connector of claim 18 wherein said tubular anchor structure is formed from an open mesh tubular framework covered with an elastic web.

* * * * *